United States Patent
Cavanaugh

(10) Patent No.: US 11,883,682 B2
(45) Date of Patent: Jan. 30, 2024

(54) ADJUSTABLE BRACHYTHERAPY TEMPLATE AND TEMPLATE HOLDER

(71) Applicant: CITY OF HOPE, Duarte, CA (US)

(72) Inventor: Sean Cavanaugh, Atlanta, GA (US)

(73) Assignee: City of Hope, Duarte, CA (US)

( * ) Notice: Subject to any disclaimer, the term of this patent is extended or adjusted under 35 U.S.C. 154(b) by 936 days.

(21) Appl. No.: 16/491,565

(22) PCT Filed: Mar. 8, 2018

(86) PCT No.: PCT/US2018/021622
§ 371 (c)(1),
(2) Date: Sep. 5, 2019

(87) PCT Pub. No.: WO2018/165480
PCT Pub. Date: Sep. 13, 2018

(65) Prior Publication Data
US 2021/0016104 A1    Jan. 21, 2021

Related U.S. Application Data

(60) Provisional application No. 62/468,506, filed on Mar. 8, 2017.

(51) Int. Cl.
*A61N 5/10* (2006.01)
*A61B 17/34* (2006.01)

(52) U.S. Cl.
CPC ........ *A61N 5/1007* (2013.01); *A61B 17/3403* (2013.01); *A61B 2017/3407* (2013.01);
(Continued)

(58) Field of Classification Search
CPC .................. A61B 8/12; A61B 17/3403; A61B 2017/3407; A61B 2017/3411;
(Continued)

(56) References Cited

U.S. PATENT DOCUMENTS

| 6,036,632 A * | 3/2000 | Whitmore, III | ..... A61N 5/1007 604/116 |
| 6,579,262 B1 * | 6/2003 | Mick | ................ A61M 37/0069 604/116 |

(Continued)

FOREIGN PATENT DOCUMENTS

| EP | 1374951 A1 * | 1/2004 | .......... A61N 5/1001 |
| EP | 1374951 A1 | 1/2004 | |

(Continued)

OTHER PUBLICATIONS

Dictionary.com. (2012). Impinge definition & meaning. Dictionary.com. Retrieved Jan. 24, 2023, from https://www.dictionary.com/browse/impinge (Year: 2012).*

(Continued)

*Primary Examiner* — Thaddeus B Cox
*Assistant Examiner* — Marc D. Honrath
(74) *Attorney, Agent, or Firm* — Mintz Levin Cohn Ferris Glovsky and Popeo, P.C.

(57) ABSTRACT

Brachytherapy templates and template holders can be adjustable relative to a patient's anatomy. One template includes a disposable portion with an aperture layer that includes first apertures and a patient contact layer that includes an adhesive on a surface thereof. The patient contact layer is formed from a flexible material. The template also includes a reusable portion that includes aperture plates. A locking mechanism can lock catheters firmly in place. One template holder includes a template compartment retainer constructed to hold a brachytherapy template, and a perineum attachment component is connected to the template compartment retainer by a connecting portion. The perineum attachment component includes a perineum attachment portion formed from a flexible material.

5 Claims, 17 Drawing Sheets

(52) U.S. Cl.
CPC ............... *A61B 2017/3411* (2013.01); *A61N 2005/1012* (2013.01)

(58) Field of Classification Search
CPC .......... A61B 2017/3413; A61N 5/1007; A61N 5/1027; A61N 2005/1012
See application file for complete search history.

(56) References Cited

U.S. PATENT DOCUMENTS

| | | | | |
|---|---|---|---|---|
| 2003/0139642 | A1* | 7/2003 | Hogendijk | A61N 5/1007 600/7 |
| 2010/0268014 | A1* | 10/2010 | Pitman | A61N 5/1049 600/7 |
| 2011/0105823 | A1* | 5/2011 | Single, Jr. | A61B 8/4209 606/1 |
| 2013/0012757 | A1* | 1/2013 | Helle | A61N 5/1007 600/7 |

FOREIGN PATENT DOCUMENTS

| | | | |
|---|---|---|---|
| EP | 2796169 A1 | 10/2014 | |
| WO | 2016007717 A1 | 1/2016 | |
| WO | WO-2016007717 A1 * | 1/2016 | ......... A61B 17/0218 |

OTHER PUBLICATIONS

EPO—Extended European Search Report for related European Application No. 18763329.2 dated Sep. 8, 2020, 7 pgs.
US/RO—Notification and International Search Report and Written Opinion of the ISA for related International Application No. PCT/US2018/021622 dated Jul. 6, 2018, 12 pgs.

* cited by examiner

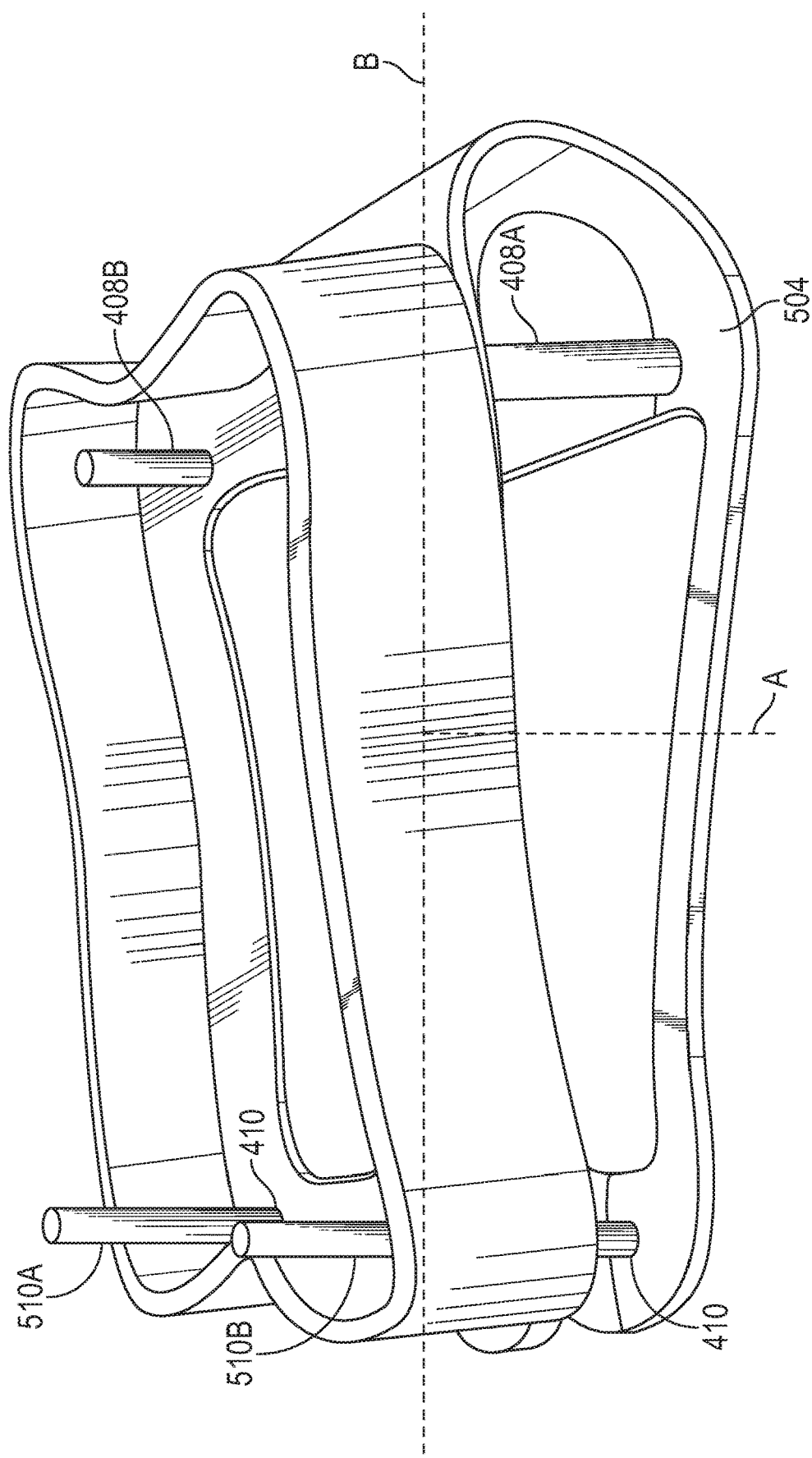

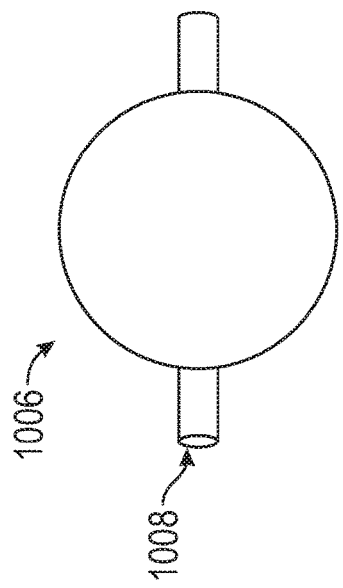
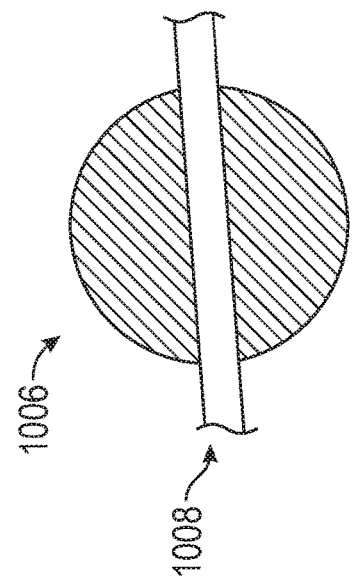
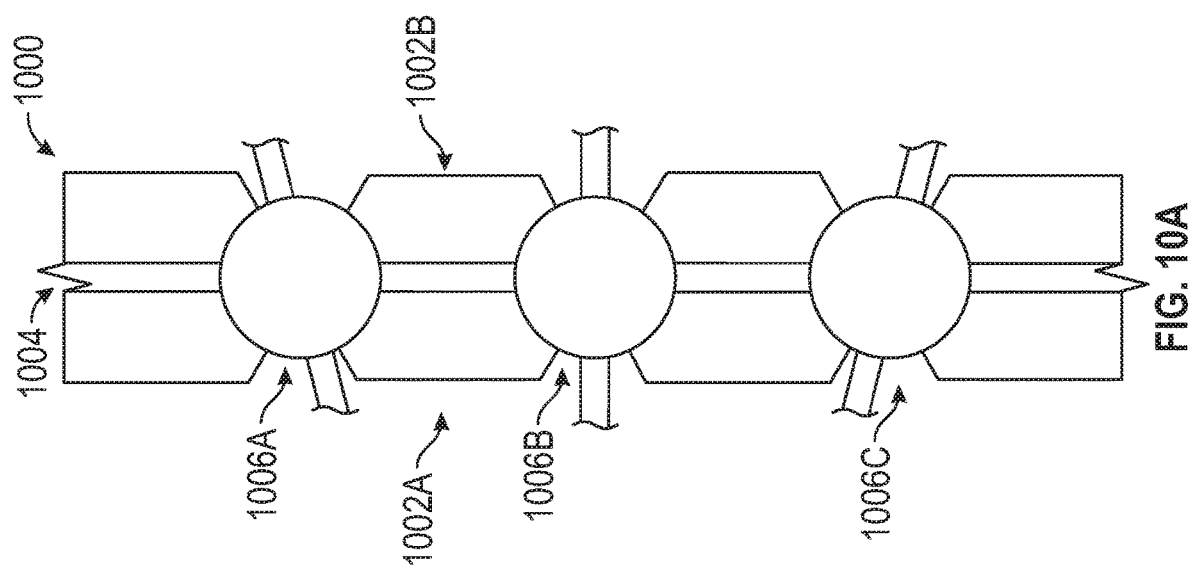

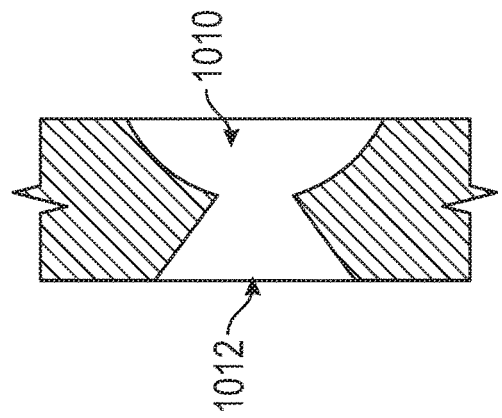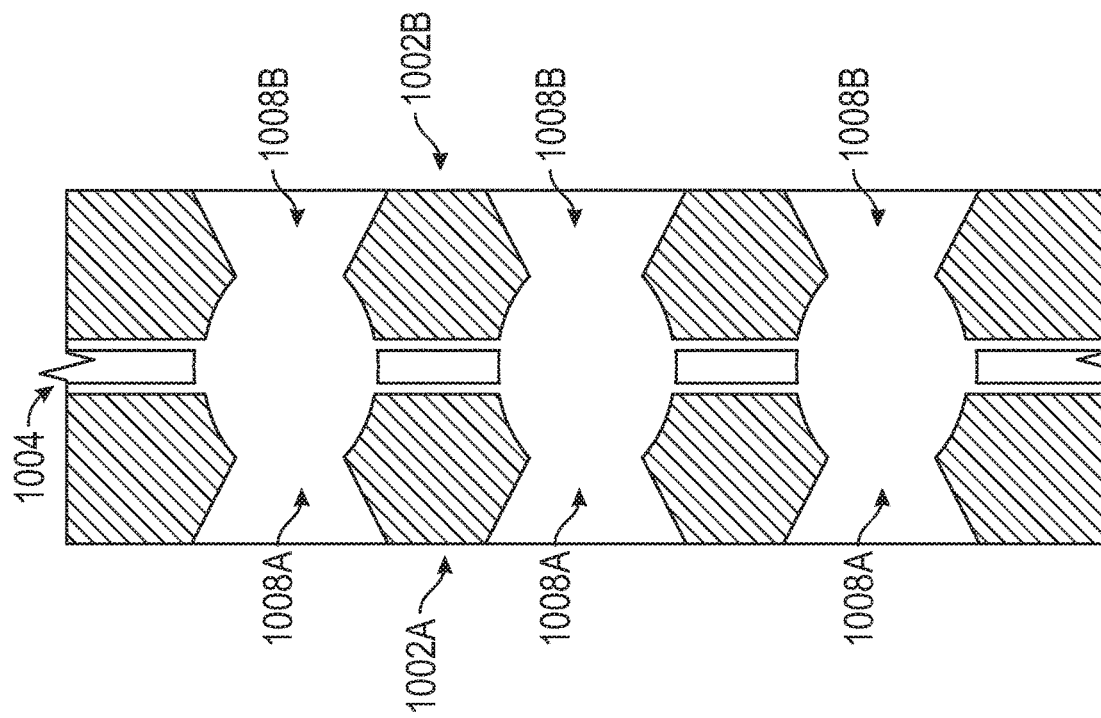

ADJUSTABLE BRACHYTHERAPY TEMPLATE AND TEMPLATE HOLDER

CROSS-REFERENCE TO RELATED APPLICATION

This application claims the benefit of U.S. Provisional Application No. 62/468,506 entitled "ADJUSTABLE BRACHYTHERAPY TEMPLATE AND TEMPLATE HOLDER," filed Mar. 8, 2017, the entirety of which is incorporated herein by reference.

TECHNICAL FIELD

The present application relates generally to adjustable brachytherapy templates and template holders.

BACKGROUND OF THE DISCLOSURE

Prostate cancer is the most common cancer diagnosed in men in the United States. In 2017, an estimated 180,000 people will be diagnosed with prostate cancer and approximately 26,000 people will die of it. For those who seek treatment, their options generally involve a selection of surgery and/or radiation. Each of these approaches, however, can carry the risk of significant side effects, including incontinence and erectile dysfunction. Prostate brachytherapy is a type of radiation treatment that carries a lower risk of side effects while maintaining high efficacy. Prostate brachytherapy is divided into two types of treatment options: low-dose rate (LDR) and high-dose rate (HDR). In HDR brachytherapy, a series of catheters are inserted into the patient's prostate and positioned near a tumor. Then, a series of radioactive pellets are inserted into the catheters. Since the dose rate is high, the pellets are only left in place for a relatively short period of time, after which the pellets are withdrawn. This procedure may be repeated the same day or on a later date. In some instances, only one round of treatment is needed and the patient may even be able to go home that same day.

To deliver the catheters to their desired positions, a rigid flat template is often used. The treatment is most effective when the position of the template is constant during the procedure. If the template moves during the procedure, the catheters may change their position or be inadvertently withdrawn, the latter of which is known as extrusion. To help avoid shifting or extrusion, the template is often sutured into place. The flat configuration of the template causes the sutures to pull and irritate the patient's skin because the template does not conform to the patient's anatomy. If the template is moved too far out of position, the planning of treatment must begin anew.

Current templates have apertures into which the catheters are inserted in parallel alignment relative to each other. However, the anatomy of the patient as well as individual extent of the tumor in a three dimensional space make a standard parallel catheter placement inadequate to optimally target all tumor regions.

Current templates also have an inadequate locking mechanism for securing the catheters. The locking mechanism is based on thumbscrews which are tightened to secure the catheters. However, over a treatment period (e.g., 12-20 hours), patient motion may cause the plates, and consequently the thumbscrews, to loosen and the catheters to move relative to each other.

In light of the above, it would be desirable to have an HDR template that conforms to a patient's anatomy to minimize the discomfort and potential for repeated procedures. It would also be desirable to have an HDR template with a better locking mechanism.

The description provided in the background section should not be assumed to be prior art merely because it is mentioned in or associated with the background section. The background section may include information that describes one or more aspects of the subject technology.

BRIEF SUMMARY OF THE DISCLOSURE

One or more of the above limitations may be diminished by templates and template holders described herein.

In one embodiment, a brachytherapy template holder is provided. The template holder includes a template compartment retainer constructed to hold a brachytherapy template and a perineum attachment component connected to the template compartment retainer by a connecting portion. The perineum attachment component includes a perineum attachment portion formed from a flexible material.

In another embodiment, a brachytherapy template is provided. The template includes a disposable portion that includes an aperture layer that includes first apertures and a patient contact layer that includes an adhesive on a surface thereof. The patient contact layer is formed from a flexible material.

In a further embodiment, a brachytherapy template is provided. The template includes a locking mechanism which locks each horizontal and/or vertical row of balls and catheters inserted therein or individual sockets and catheters firmly in place.

In yet another embodiment, a brachytherapy template is provided. The template includes first layers, a second layer and needle guides. Each of the first layers includes first apertures. The second layer is arranged between the first layers and includes second apertures. The first apertures and the second apertures define sockets. The needle guides are respectively disposed in the sockets and are pivotable by about ±20° relative to a longitudinal axis extending from a surface of one of the first layers.

The description in this summary section may provide some illustrative examples of the disclosure. This section is not intended to be a broad overview or to identify essential elements of the disclosure.

BRIEF DESCRIPTION OF THE DRAWINGS

FIGS. 4A and 4B show illustrations of an adjustable template holder.

FIG. 10A shows a multilayered brachytherapy template according to one embodiment.

FIG. 10B shows an illustration of a needle guide.

FIG. 10C shows a cross-sectional illustration of the needle guide shown in FIG. 10B.

FIG. 11A shows an illustration of the multilayered brachytherapy template shown in FIG. 10A with the needle guides removed.

FIG. 11B shows an illustration of an aperture formed in a first layer of the multilayered template.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

In accordance with example aspects described herein, templates and template holders for brachytherapy are provided.

Figure 1:
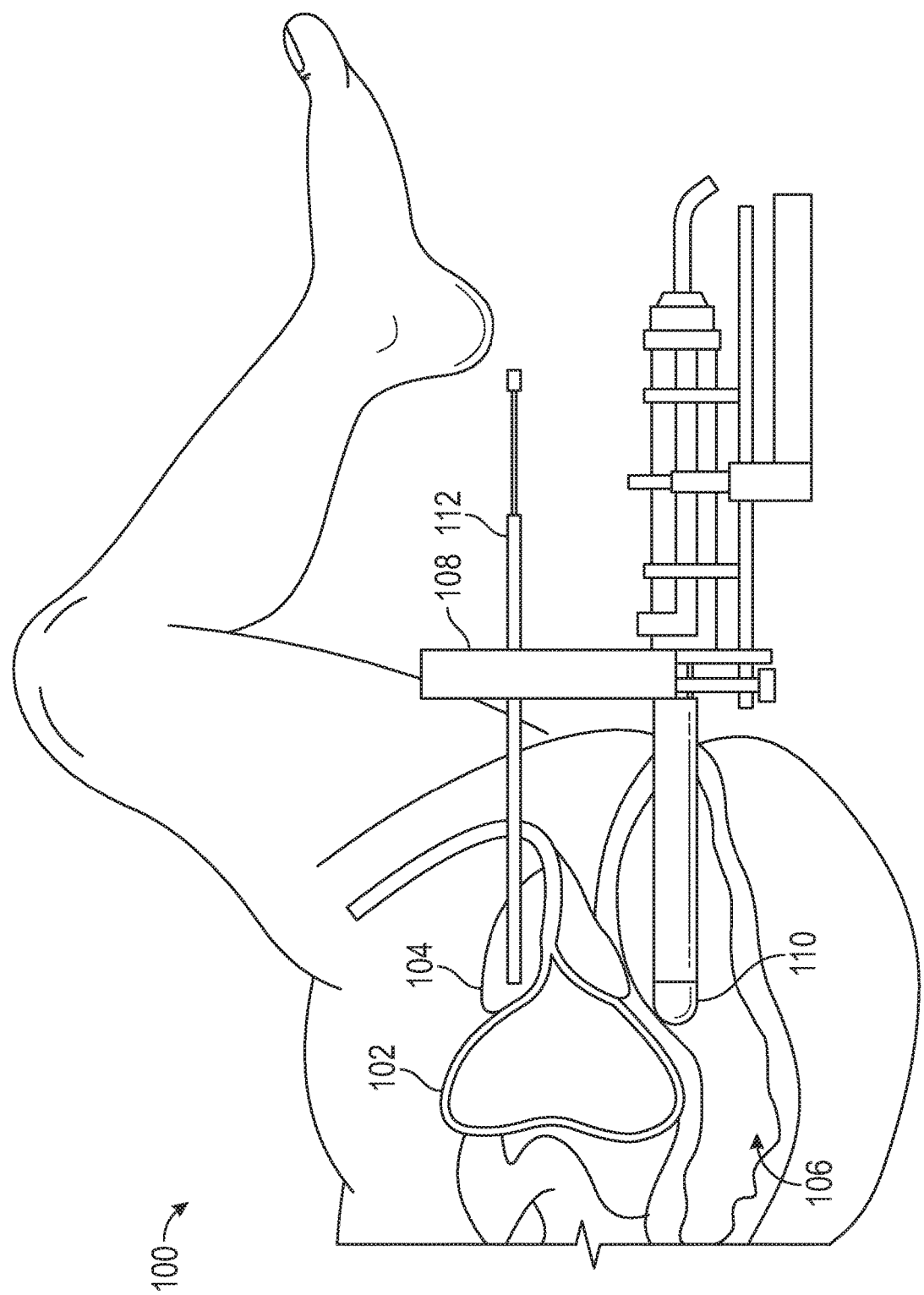
FIG. 1 shows an anatomical illustration of a prostate brachytherapy procedure.

FIG. 1 is an anatomical cross-section illustration showing a prostate brachytherapy procedure. A patient 100 is positioned supine with his legs relaxed to the sides and his perineum area exposed. Typically, an ultrasonic probe 110 is inserted into the patient's rectum 106 and positioned near the prostate 104. The probe 110 is used to identify the location of a treatment area (e.g., an area that includes a tumor) within the prostate 104. Catheters 112 are inserted into the template 108 according to a treatment plan. The treatment plan is generated before the procedure begins based on the size and location of the tumor, the patient's anatomy, and the positioning capabilities of the template. As discussed below, in one embodiment, an exemplary template may include a plurality of pivotable apertures that allow for off-axis insertion of a catheter. The off-axis insertions provide additional degrees of freedom. As such, the computer calculates the treatment plan based, in part, on the additional degrees of freedom, which may reduce the size of the radioactive dose required. Once the catheters 112 are in position, radioactive pellets are inserted into the catheters 112 and delivered to the treatment site. While the positioning of the catheters 112 could be done by either a computer or a person, the loading of the radioactive pellets is typically controlled by a computer based on data from the probe 110. This eliminates the need for the technician to be exposed to unnecessary radiation.

Figure 2:
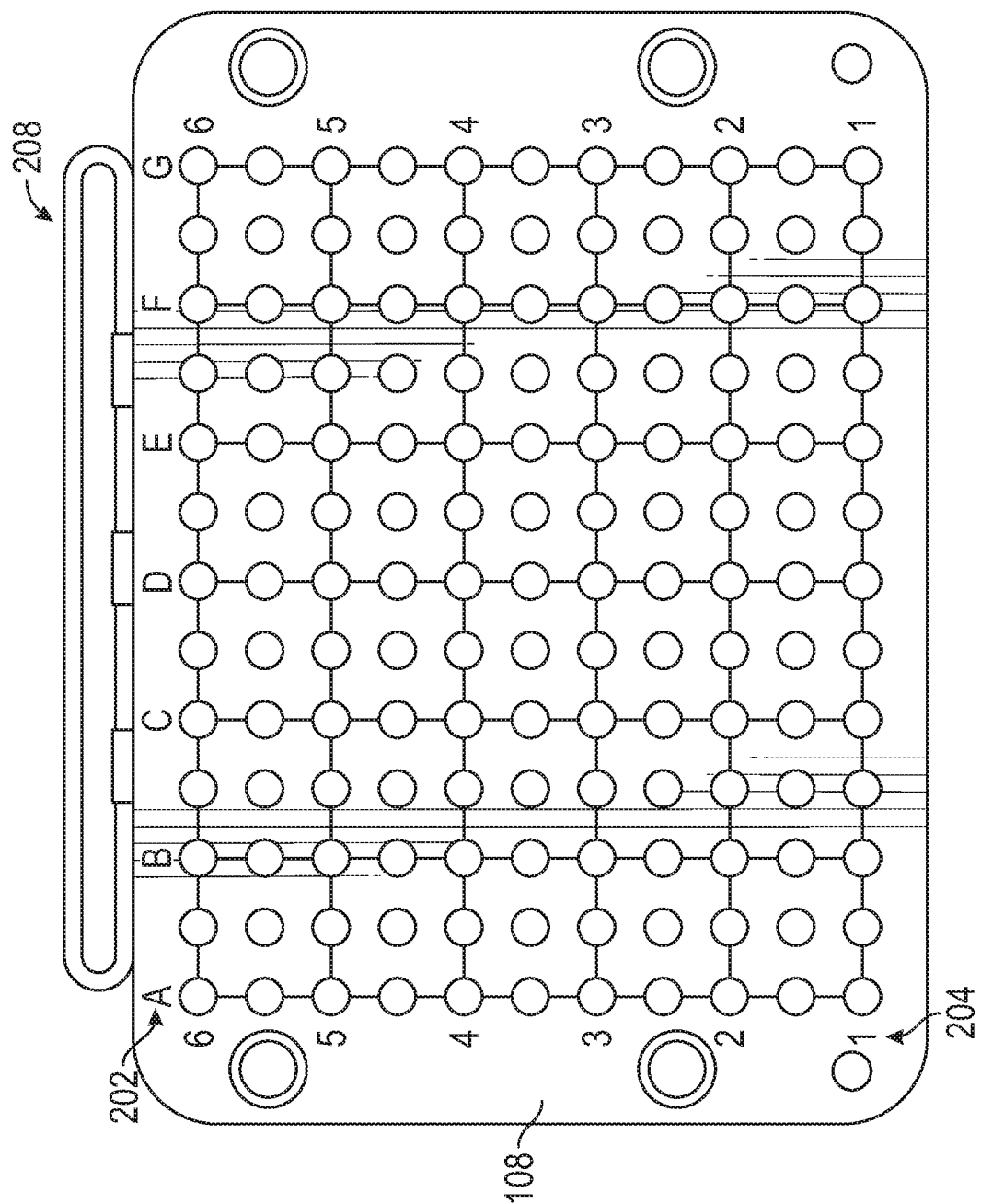
FIG. 2 shows an illustration of a brachytherapy template.

FIG. 2 illustrates a template 108. The template may have rows 202 designated by letters, and columns 204 designated by numbers. In this particular template 108, the total number of apertures is 143 (11×13). Depending on the size of the patient, the template 108 may be a different size with a different number of apertures. A rail 208 is provided that may be connected to a cam system or a gear system (located in housing 914 and described in greater detail below). The template 108 may be formed from a plurality of plates (each of which includes a same number of apertures) that are movable relative to each other. Rail 208 is connected to the plurality of plates and thus, through the cam or gear system, the plurality of plates may be moved.

Figure 3:
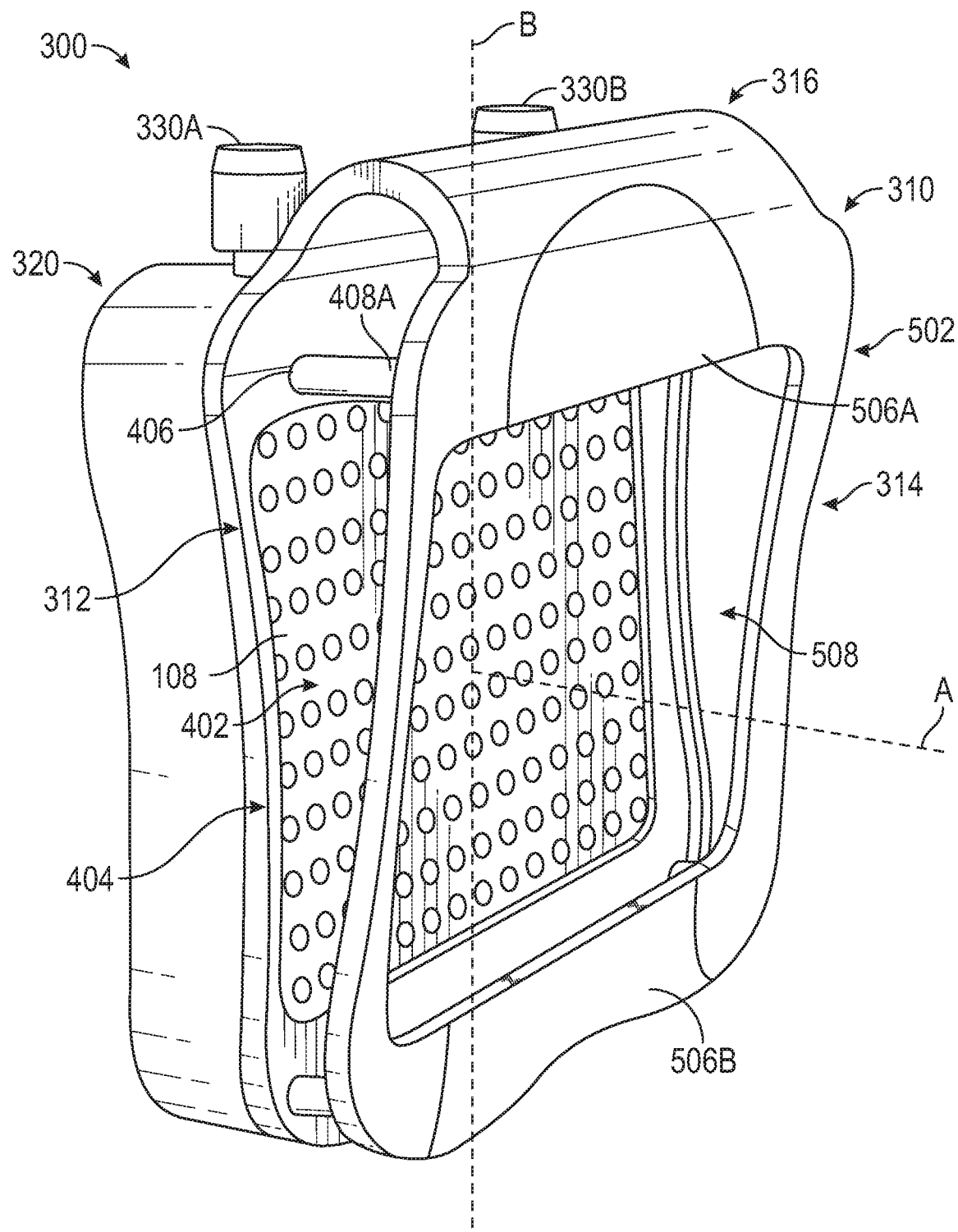
FIG. 3 shows an illustration of a brachytherapy template loaded into an adjustable template holder.

FIG. 3 is an illustration of a template 108 loaded into an adjustable template holder 300, according to one embodiment. Template holder 300 can be divided into three main components: a perineum attachment component 310, a template compartment 320, and a pair of locking knobs 330A and 330B.

The locking knobs 330A and 330B may be connected to a cam system or a gear system such that rotation of the locking knobs 330A and 330B causes at least two of the plurality of plates in template 108 to move relative to each other. The relative movement may narrow the size of the apertures provided in the template 108. Thus, a catheter inserted into one of the apertures provided in the template 108 may be constricted by the relative movement of the plurality of plates and thereby secured. The cam system and gear system can be configured to require additional input to allow further movement of the plurality of plates, and thus not loosen in the manner that thumbscrews may.

The perineum attachment component 310 can be further divided into three main portions: a template compartment retainer 312, a perineum attachment portion 314, and a connecting portion 316 connecting the template compartment retainer 312 and the perineum attachment portion 314, as illustrated in FIG. 3.

As shown in FIG. 3, the template compartment retainer 312 is designed to engage the template compartment 320 and thereby attach the perineum attachment component 310 to the template compartment 320. A snap-fit connection may be used for this purpose, whereby the template compartment retainer 312 includes one or more male or female components that is positioned to engage a corresponding male or female component (as the case may be) located on the template compartment 320. The template compartment retainer 312 may have a cross-sectional profile that matches the cross-sectional profile of the template compartment 320 such that when the template compartment retainer 312 and the template compartment 320 are engaged to each other the sides are flush. Alternatively, in another embodiment, the perineum attachment component 310 and the template compartment 320 may be formed as a single unit.

The template compartment retainer 312 may have an opening 402 such that the template 108 is exposed when mounted inside the holder 300. The flange 404 defines the size of the opening 402. While the outer circumferential surface of flange 404 may be rectangular in shape, it need not be. For example, as shown in FIG. 3, the outer circumferential surface of flange 404 has an hourglass cross-sectional profile in a direction perpendicular to axis A. Axis A is substantially normal to the surface of a template 108 when mounted in the template holder 300. While the outer circumferential profile of flange 404, in FIG. 3, is an hourglass shape, the interior circumferential surface which defines opening 402 is generally rectangular with rounded corners. Thus, in one embodiment, the outer circumferential surface of flange 404 adopts an hourglass shape that may provide a better fit relative to a patient's body while the interior circumferential surface is rectangular so as to accommodate the grid layout of template 108.

Figure 4B:
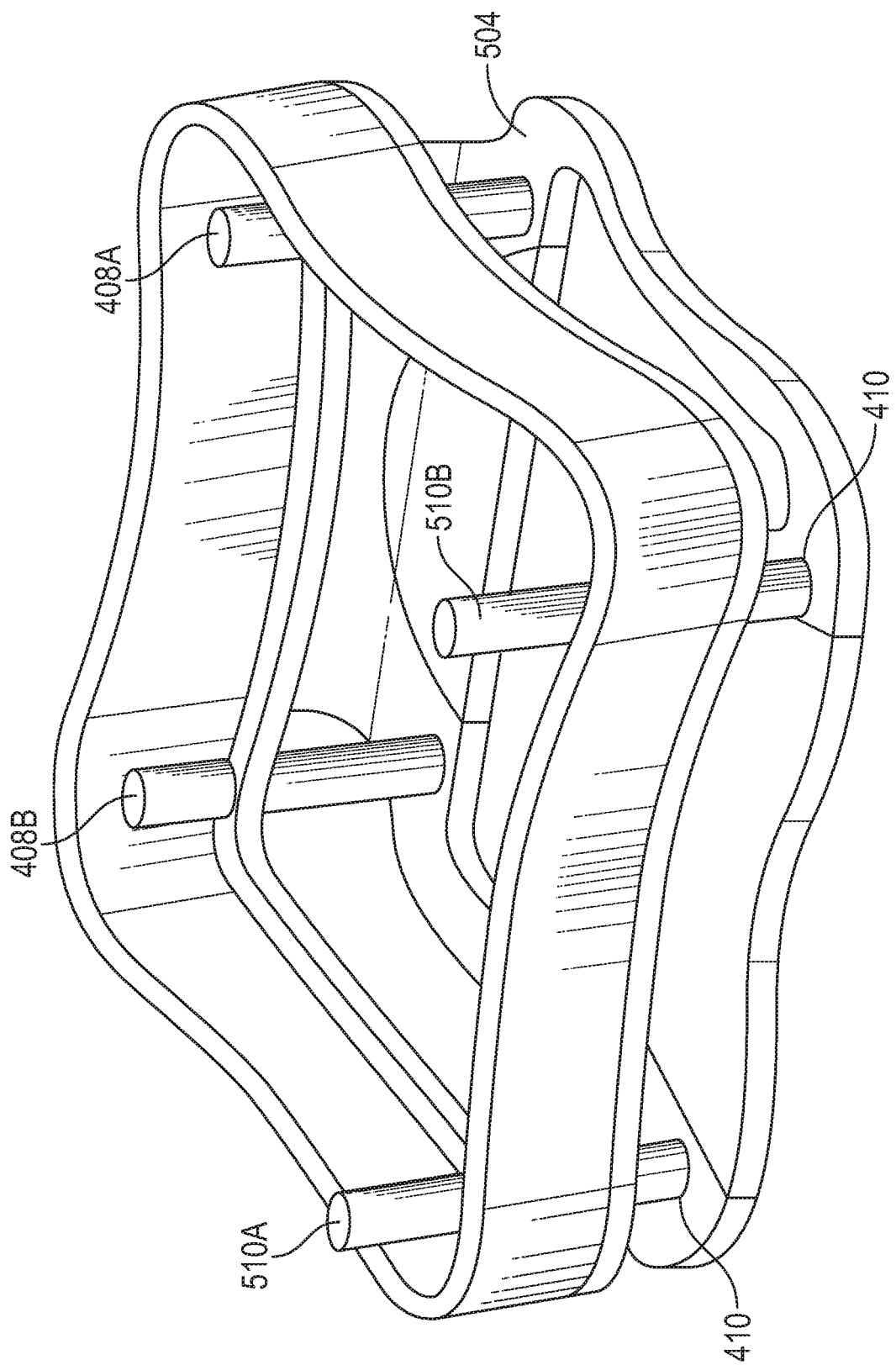

The template compartment retainer 312 may also include one or more first apertures 406 through which a first pair of displacing rods 408A-B may be inserted. FIGS. 3, 4A, and 4B illustrate an embodiment with a first pair of displacing rods 408A and 408B. The first pair of displacing rods 408A and 408B may be connected to the perineum attachment portion 314 of the perineum attachment component 310. Thus, translation of the first pair of displacing rods 408A and 408B into or out of the respective first apertures 406 may cause the perineum attachment portion 314 to be displaced towards or away from the template compartment retainer 312. As discussed below, the connecting portion 316 may act as a spring over a certain displacement range of the perineum attachment portion 314 relative to the template compartment retainer 312. Thus, when the perineum attachment portion 314 is disposed within this range, the perineum attachment portion 314 will be biased away from the template compartment retainer 312. To prevent such displacement, a lock nut (or other fasteners) may also be provided that secures the first pair of displacing rods 408A and 408B relative to the first apertures 406 preventing relative motion of the perineum attachment portion 314 with respect to the template compartment retainer 312.

The template compartment retainer 312 may include second apertures 410 for receiving a second pair of displacing rods 510A and 510B, as shown in FIGS. 4A and 4B. Like the first pair of displacing rods 408A and 408B, the second pair of displacing rods 510A and 510B are connected to the perineum attachment portion 314. Translation of the second pair of displacing rods 510A and 510B may also cause the perineum attachment portion 314 to be displaced towards or away from the template compartment retainer 312. Thus, lock nuts (or other fasteners) may be provided and secure the second pair of displacing rods 510A and 510B relative to the respective second apertures 410.

As shown in FIGS. 3, 4A, and 4B, the perineum attachment portion 314 includes an outer side 502 and inner side 504. The outer side 502 includes two adhesive application areas 506A and 506B. Areas 506A and 506B are formed from, in one embodiment, a plastic that bonds with an adhesive that also bonds with human skin. Thus, by applying adhesive to the adhesive application area 506A and 506B the perineum attachment portion 314 may be affixed to a patient. The perineum attachment portion 314 may be a curved surface that generally conforms to a patient's anatomy. The perineum attachment portion 314 may also be formed from a flexible material that may elastically deform when pressed against a patient's skin, e.g. silicone. By such deformation a greater surface area of the perineum attachment portion 314 may be in contact with the patient than if the material was inelastic. One advantage of this flexibility is that the perineum attachment portion 314 may deform to match a curvature of the patient's body, thus making the perineum attachment portion 314 adaptable to different patients and less likely to move during the procedure. Moreover, since the perineum attachment portion 314 is affixed to the patient using an adhesive (e.g., a gel adhesive), rather than suturing, the patient will not experience the pain and irritation associated with sutured templates. Additionally, or as an alternative, a harness may be used to secure the template.

Like the template compartment retainer 312, the perineum attachment portion 314 includes an opening 508. The perineum attachment portion opening 508 is at least as large as the template compartment retainer opening 402 and a center of opening 508 is substantially coaxial with a center of opening 402. This arrangement allows for catheters 112 to pass through the perineum attachment portion opening 508 and the template compartment retainer opening 402 and engage the template 108 unencumbered.

The inner side of the perineum attachment portion 314 may have the first pair of displacing rods 408A and 408B and the second pair of displacing rods 510A and 510B embedded therein.

The template compartment retainer 312 and the perineum attachment portion 314 are connected by the connecting portion 316 in a generally u-shaped manner. By virtue of this shape, the connecting portion 316 resists the relative motion of the perineum attachment portion 314 away from the template compartment retainer 312, beginning from an a static arrangement.

Figure 5:
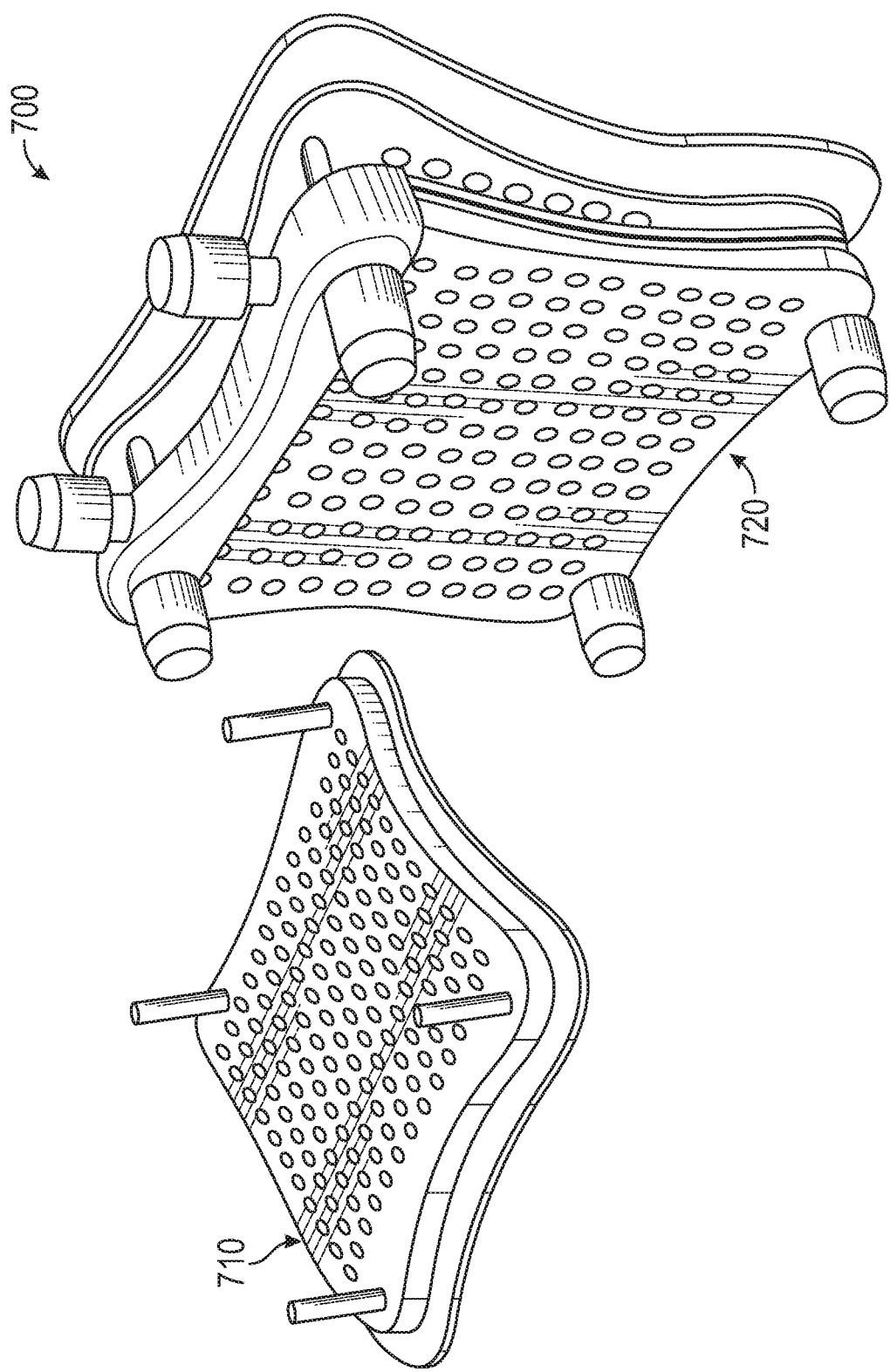
FIG. 5 shows another embodiment of an adjustable brachytherapy template.

FIGS. 5-7B illustrate a template 700 according to another embodiment. As shown in FIG. 5, the template 700 includes a disposable portion 710 that may be connected to a reusable portion 720. The disposable portion 710 is shown in further detail in FIG. 6. The reusable portion 720 is shown in further detail in FIGS. 7A-B.

Figure 6:
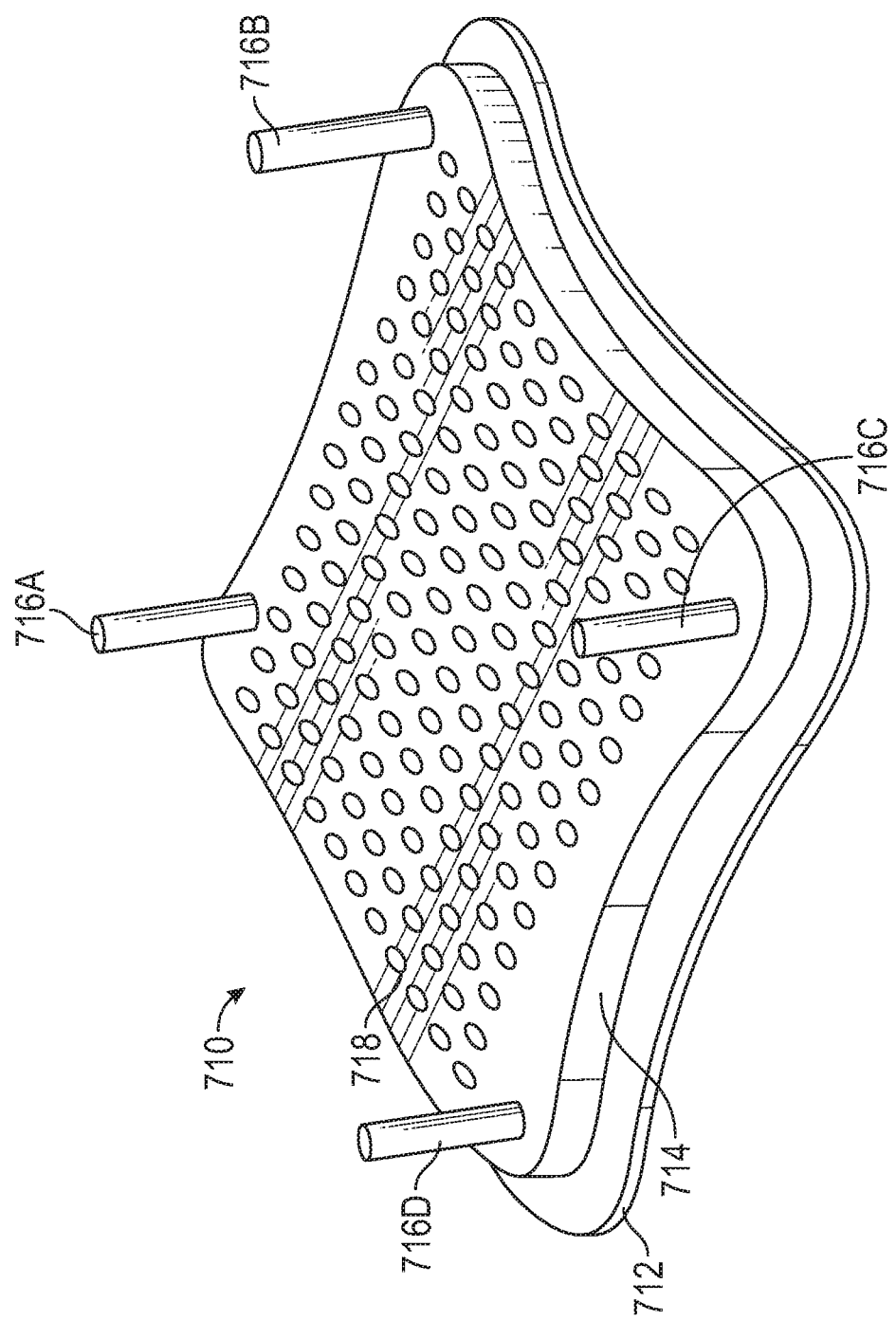
FIG. 6 shows a disposable portion of the adjustable brachytherapy template illustrated in FIG. 5.

FIG. 6 illustrates the disposable portion 710 of the template 700. The disposable portion 710 of the template 700 may include two layers: a patient contact layer 712 and an aperture layer 714. The patient contact layer 712 may be formed of a flexible material and contain an adhesive on a side opposite from the side that joins the aperture layer 714. The adhesive may be covered by a film of a nonreactive material so as not to form a bond prior to placing the patient contact layer 712 on the patient. Once the film is removed, the patient contact layer 712 may be placed on the patient and at which point the adhesive will bond the disposable portion 710 of the template 700 to the patient. After the treatment is complete, the bond may be dissolved by a solvent.

Connected to the patient contact layer 712 is the aperture layer 714. The aperture layer 714 may, in one embodiment, be connected to the patient contact layer 712 by a permanent adhesive so as to form a single structure. The aperture layer 714 may include a plurality of attachment posts 716A-D. The attachment posts 716A-D provide for a mechanical connection between the disposable portion 710 and the reusable portion 720. As described below, the attachments post 716A-D may engage corresponding receptacles in the reusable portion 720. The aperture layer 714 also includes a plurality of apertures 718 each of which is sized to receive a catheter 112.

The aperture layer 714 may be formed from a flexible material. In one embodiment, the material has a greater resistance to displacement (i.e., is stiffer) in a direction parallel to the plane of the aperture layer 714. If a catheter 112 is inserted into an aperture 718 at a substantial angle (e.g., >10°), and thus imparts a force in a direction parallel to the plane of the aperture layer, the material will have sufficient stiffness to resist a deformation in the same direction. This prevents the aperture 718 from being inadvertently widened when a catheter is inserted into it. However, material of the aperture layer 714 may be easily deformable in a direction perpendicular to a surface thereof. Thus, when the disposable portion 710 is placed firmly against a patient's skin, the aperture layer 714 may deform so as to match a contour of the patient's anatomy.

Figure 7A:
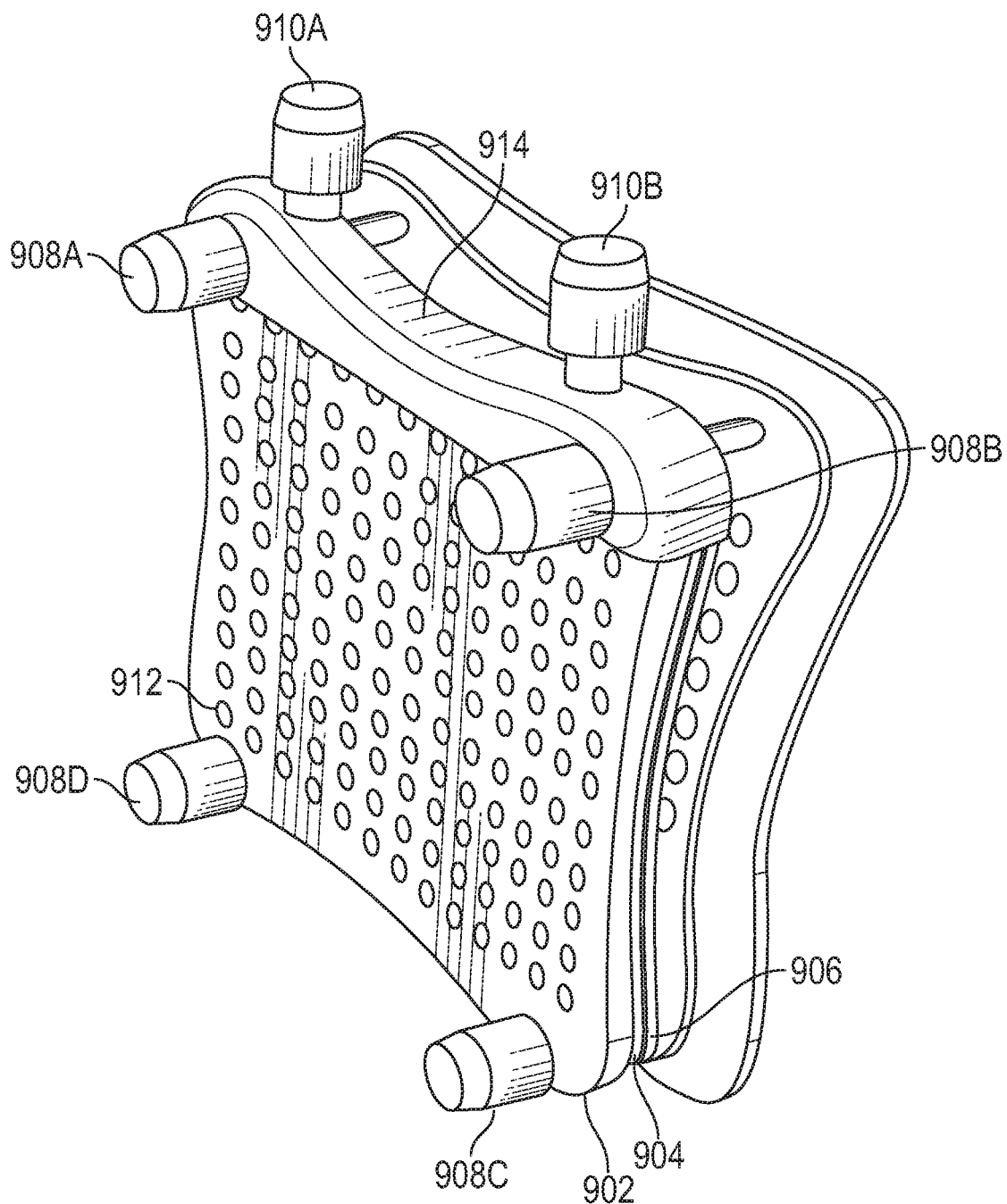
FIGS. 7A and 7B show a reusable portion of an adjustable brachytherapy template in FIG. 5.
Figure 7B:
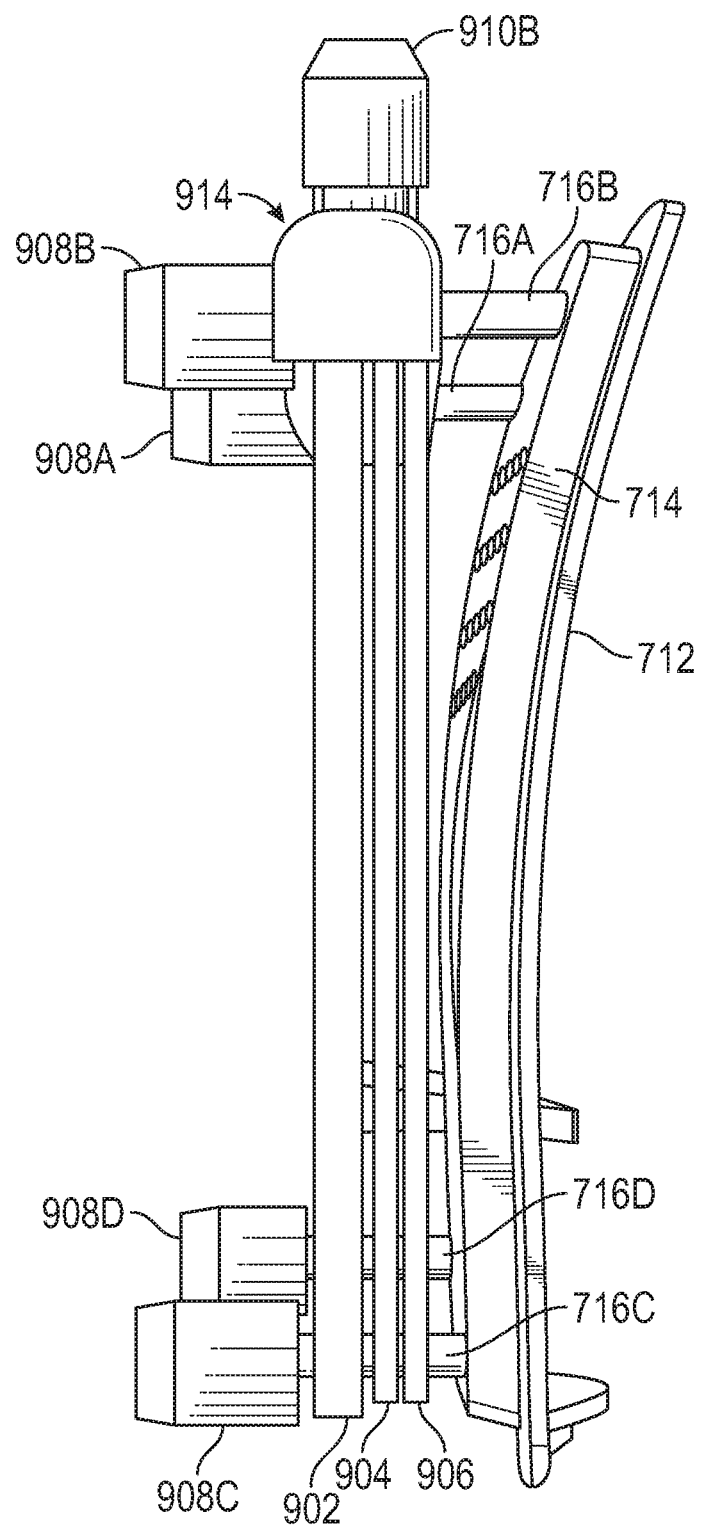

FIGS. 7A-7B illustrates the disposable portion 710 attached to the reusable portion 720. The reusable portion 720 includes a first aperture plate 902, a second aperture plate 904, and a third aperture plate 906. The second aperture plate 904 and the third aperture plate 906 may be thinner than the first aperture plate 902 and movable in a direction substantially perpendicular to the depth direction of the apertures 912. Such relative movement effectively narrows the apertures in these plates, thus constricting any catheters 112 mounted therein. Relative adjustment of the second aperture plate 904 to the third aperture plate 906 may be done via locking knobs 910A and 910B.

Locking knob 910A may, in one embodiment, be connected to a cam system (located in housing 914) such that rotation of the locking knob 910A causes the second aperture plate 904 to be displaced in the direction substantially perpendicular to the depth direction of the apertures in the second aperture plate 904. Once locking knob 910A is fully rotated, the cam system reaches the engaged position and the second aperture plate 904 is at a maximum displacement. At this position, additional rotational force must be applied to locking knob 910A to release the second aperture plate 904 from the locked position. As such, there is a natural resistance to any tendency for the second aperture plate 904 to be displaced should a force be imparted to the catheter 112 (e.g., by patient movement). The level of resistance can be dictated by the dimensions of the cam system, but should be sufficient to prevent forces that may be exerted on the second aperture plate 904 by unintentional motion of the patient from causing a displacement of the second aperture plate 904.

Similarly, locking knob 910B may also, in one embodiment, be connected to a cam system (located in housing 914) such that rotation of the locking knob 910B causes the third aperture plate 906 to be displaced in the direction substantially perpendicular to the depth direction of the apertures in the third aperture plate 906. Once locking knob 910B is fully rotated, the cam system reaches the engaged position and the third aperture plate 906 is at a maximum displacement. At this position, additional rotational force must be applied to locking knob 910B to release the third aperture plate 906 from the locked position. As such, there is a natural resistance to any tendency for the third aperture plate 906 to be displaced should a force be imparted to the catheter 112 (e.g., by patient movement). The level of resistance can be dictated by the dimensions of the cam system, but should be sufficient to prevent forces that may be exerted on the third aperture plate 906 by unintentional motion of the patient from causing a displacement of the third aperture plate 906.

The cam system is merely one method of controlling the displacement of second aperture plate 904 and the third aperture plate 906. Alternatively, a gear system may be employed. In this case, locking knobs 910A and 910B may be biased by springs to an upright position where they are disengaged from the gear system. The second aperture plate 904 and the third aperture plate 906 may be connected to the gear system to allow for their respective displacements. However, when the locking knobs 910A and 910B are biased by the springs into an elevated position, they are disengaged from the gear system effectively disabling the gear system and preventing any displacement of the second aperture plate 904 and the third aperture plate 906. Only when the locking knobs 910A and 910B are biased against the springs such that they engage the gear system are the second aperture plate 904 and the third aperture plate 906 movable. As such, this system ensures that the second aperture plate 904 and the third aperture plate 906 cannot be moved unless such movement is intended.

As mentioned above, the attachment posts 716A-D may be received by receptacles on the reusable portion. A plurality of receptacles may be provided in the form of holes passing through the first, second, and third aperture plates (902, 904, and 906). As shown in FIGS. 7A-B, in one embodiment, two of the plurality of receptacles may also pass through the housing 914. The posts 716A-D and the receptacles may be threaded such that rotation of the posts 716A-D advances or retracts the posts 716A-D relative to the receptacle. Posts 716A-D may be detachably connected to adjustment knobs 908A-D, respectively. By rotating adjustment knobs 908A-D, the posts 716A-D may be advanced or retracted from the receptacles. As such, by manipulating adjustment knobs 908A-D, the reusable portion 720 may be adjusted relative to the disposable portion 710. Thus, once the disposable portion 710 is affixed to the patient, the reusable portion 720 may be connected to the disposable portion 710 and adjusted relative to the disposable portion such that apertures 912 in the reusable portion and the apertures 718 in the disposable portion are brought into coaxial alignment. Once aligned, a catheter can be inserted into the apertures 912 and 718, with locking knobs 910A and 910B used to engage either the cam system or the gear system to lock the catheter into position, such that the catheter will not be deflected from an intended course during treatment.

The first aperture plate 902 contains a plurality of apertures 912 sized to receive catheters 112. As the first aperture plate 902 is not intended to be affixed to the patient, it may be made from either a rigid material or a flexible material. In the embodiment shown in FIGS. 7A-B, the apertures 912 are holes in the first aperture plate 902. However, in one embodiment, the apertures 912 may be formed by a ball-and-socket joint, as illustrated in FIG. 8.

Figure 8:
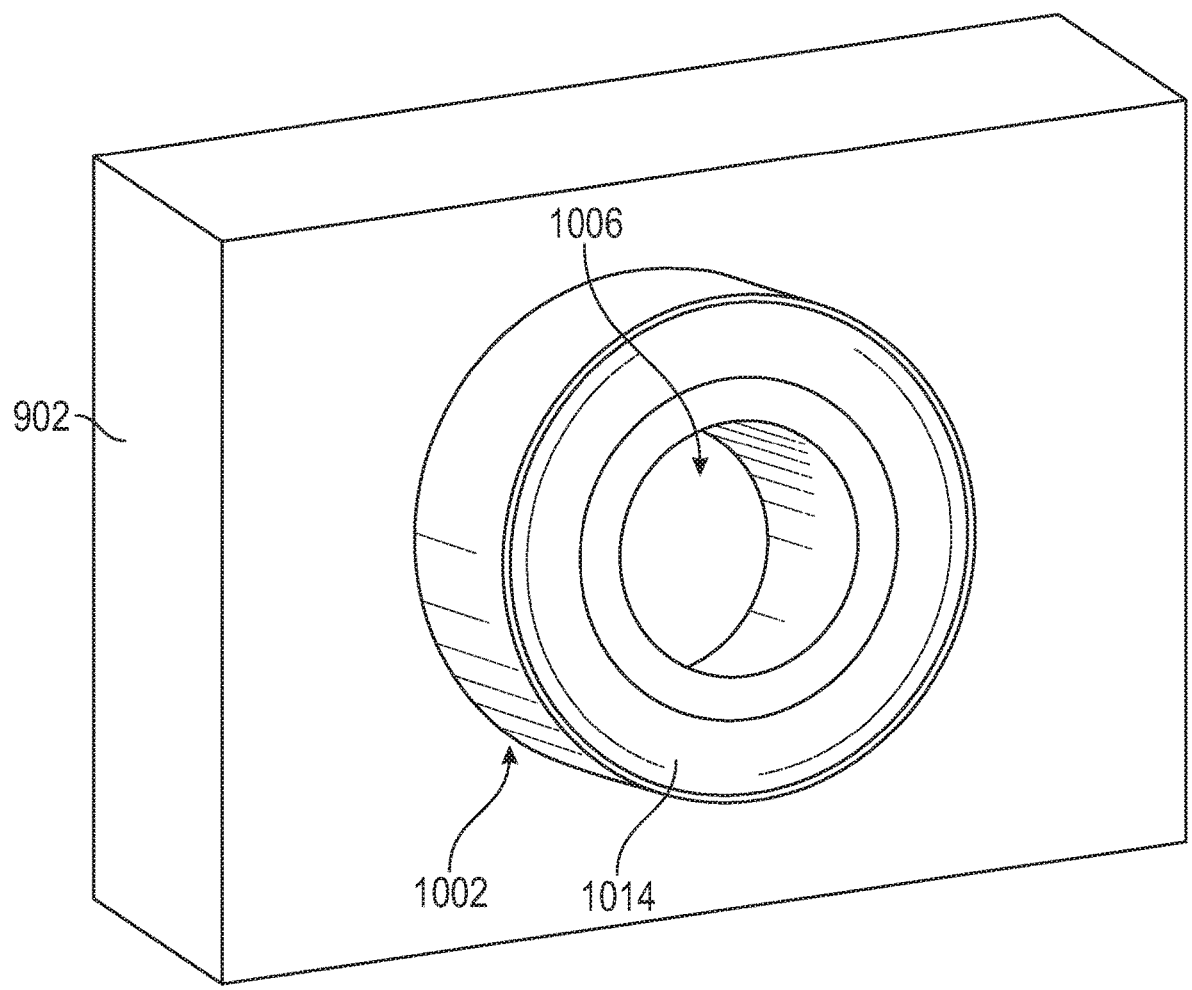
FIG. 8 shows an exemplary ball and socket aperture.

FIG. 8 is an illustration of exemplary aperture formed from a ball-and-socket joint. A portion of the first aperture plate 902 is shown with a socket 1002 protruding slightly therefrom. This is an exemplary arrangement, as the socket 1002 may be entirely contained within the first aperture plate 902. Within socket 1002 a ball 1014 is contained and displaceable over a prescribed angular range (e.g., ±20°), with respect to the longitudinal axis of a cylindrical opening 1006 in the ball 1014 in a non-displaced position. The cylindrical opening 1006 is dimensioned to receive the catheter 112. As such, by this arrangement the catheter 112 may be displaced over the prescribed angular range. This allows for radioactive pellets, placed inside of catheter 112 during treatment, to be placed off-axis relative to another catheter. A computer planning the treatment course can take into account the displaceability of the catheter 112 in determining where the catheters should be placed. The computer may therefore consider an additional degree of freedom when planning the treatment. This additional degree of freedom may allow for closer placement of the catheter 112 to the treatment area, in consideration of patient anatomy and the three-dimensional orientation of the tumor relative to patient anatomy, thus making treatment more aligned with individual patient requirements, reducing the radiation dose, the number of treatment sessions, and the length of the treatment sessions. In addition, this additional degree of freedom in positioning the catheters 112 may allow for patients who, based on conventional techniques, were not candidates for HDR brachytherapy to otherwise become candidates. In prostate brachytherapy, the catheters 112 must avoid the patient's urethra and pubic bone. If the pubic bone is too low, the patient may be ineligible for HD brachytherapy because the needles would bend when they hit bone structure.

Figure 9:
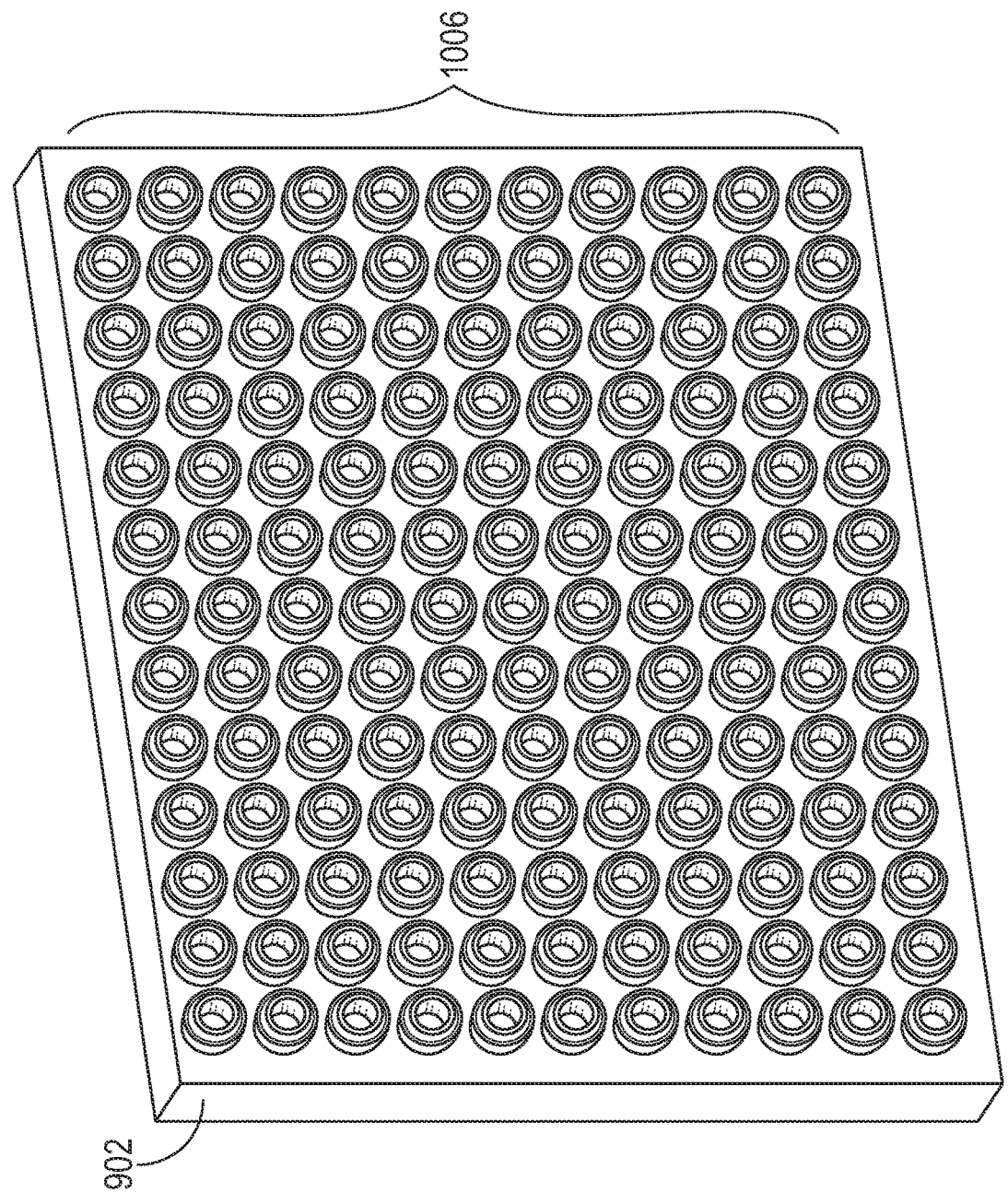
FIG. 9 shows a brachytherapy template with ball and socket apertures.

FIG. 9 is an illustration of a first aperture plate containing a plurality of cylindrical openings 1006, each of which is displaceable by the prescribed angular range. In this example, 11 rows and 13 columns of displaceable openings 1006 are provided, which matches the number of apertures shown in the template 108 in FIG. 2. The use of the first aperture plate shown in FIG. 9 may render the second and third aperture plates 904 and 906 superfluous and allow for their removal. Since the template features a locking mechanism that adequately locks each horizontal and/or vertical row of sockets (or individual socket) so that the catheters are held firmly in place, there is no need for additional plates that are movable relative to the first aperture plate 902. The template shown in FIG. 9 may be used in conjunction with the template holder 300 depicted in FIG. 3. In this case, locking knobs 330A and 330B may be used to lock horizontal and/or vertical rows to the openings 1006.

In yet another embodiment, an exemplary locking system that makes use of multiple plates and a spring biasing system is provided and will now be described with references to FIGS. 10A-15.

FIG. 10A is a cross-sectional view of a multilayered template 1000 according to one embodiment. The template 1000 includes first layers 1002A and 1002B, a second layer 1004 disposed between the first layers 1002A and 1002B, and a plurality of needle guides 1006A-C. The needle guides 1006A-C are disposed in respective sockets defined by apertures in the first layers 1002A and 1002B and the second layer 1004. As shown in FIG. 10A, needle guides 1006A-C are generally spherical and may be made from a deformable material, e.g. plastic. As shown in FIGS. 10B and 10C, each needle guide 1006 includes a needle insertion cylinder 1008. The needle insertion cylinder 1008 may be sized to receive a 15 or 18 gauge needle and is fixed relative to the needle guide 1006, such that the needle insertion cylinder 1008 does not move relative to the needle guide 1006 when a corresponding needle is inserted therein.

As shown in FIG. 10A the needle guides 1006A-C are pivotable ±20° with respect to a zero position that is perpendicular to the surfaces of first layers 1002A and 1002B. The needle guide 1006B is disposed in the 0° degree orientation in FIG. 10A, while the needle guides 1006A and 1006C are disposed at the +20° and −20° respectively.

FIG. 11A is an illustration of the multilayered template 1000 with the needle guides 1006 removed so that apertures 1008A and 1008B respectively corresponding to first layers 1002A and 1002B can be seen. As shown in FIG. 11B, the apertures 1008A can be divided into two portions: a partially spherical section 1010 and a conical section 1012. The partially spherical section 1010 may be formed by a spherical drill bit that removes material from one side of the first layer 1002A. Similarly, the conical section 1012 may be formed by a conical drill bit that removes material from the other side of the first layer 1002A. According to one embodiment, the apertures 1008B are symmetrical to the apertures 1008A with respect to a plane defined by second layer 1004, and thus may be formed by the same process described above with respect to the apertures 1008A.

Figure 12A:
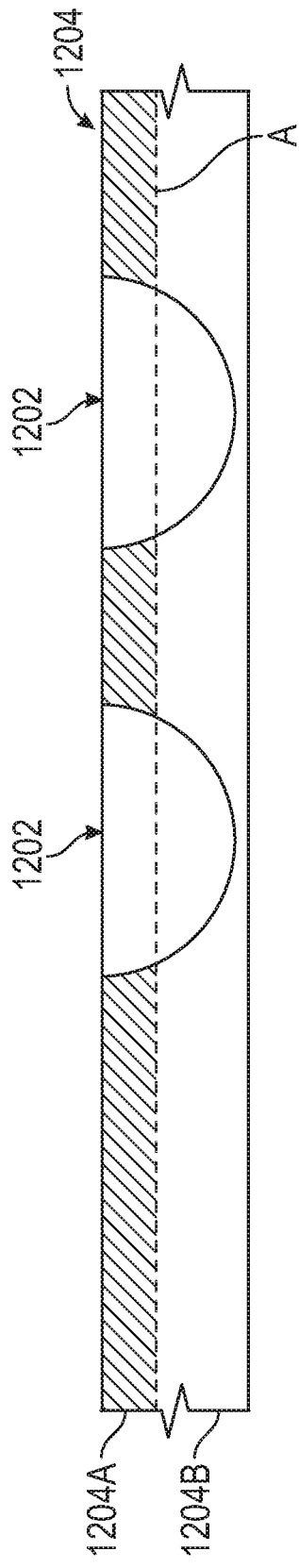
FIGS. 12A, 12B, and 12C show the formation of a second layer of the multilayered template.
Figure 12B:
Figure 12C:
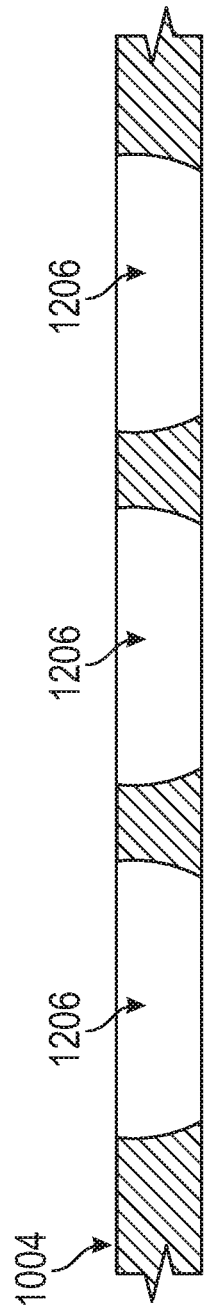

FIGS. 12A-12C depict the formation of the second layer 1004. First, as shown in FIG. 12A, a spherical drill bit is used to form a plurality of spherical depressions 1202 in a substrate 1204. Next, an upper portion 1204A of the substrate 1204 is separated from a lower portion 1204B of substrate 1204, as indicated by the dashed line A in FIG. 12A. As shown in FIG. 12B, the separated upper portion (identified as 1204-1A in FIG. 12B) is then adhered to another separated upper portion (identified as 1204-2A in FIG. 12B) that was created in the same manner as upper portion 1204A. Separated upper portion 1204-2A, however, is inverted 180° with respect to 1204-1A across a plane of symmetry defined by the bond between the two upper portions 1204-1A and 1204-2A. Thus, as shown in FIG. 12C, the two separated upper portions 1204-1A and 1204-2A now form the second layer 1004 with a plurality of apertures 1206 forming at the mid-line of a sphere.

Figure 13B:
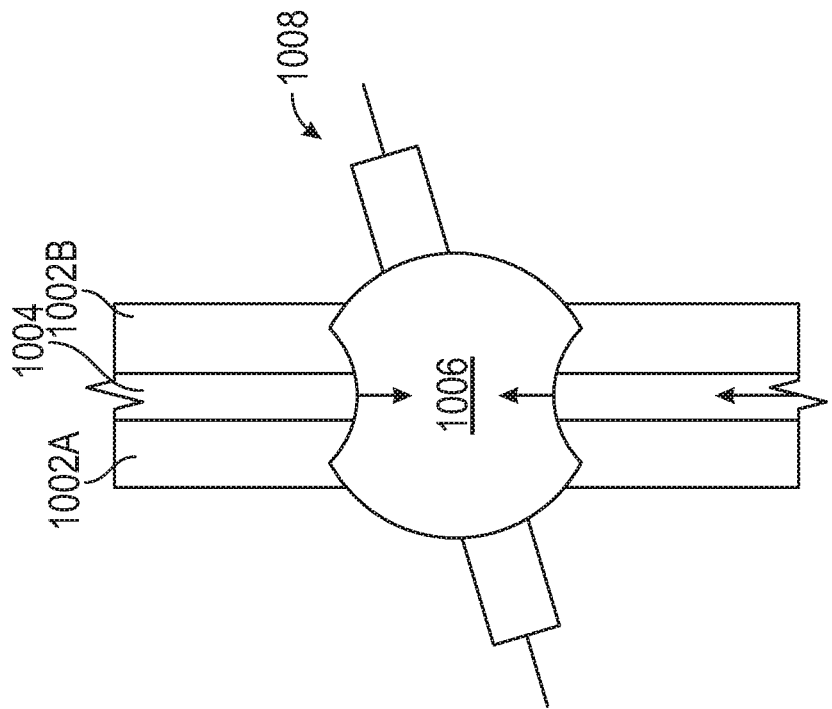
FIGS. 13A and 13B show a locked state and an unlocked state of the needle guide shown in FIG. 10B.
Figure 13A:
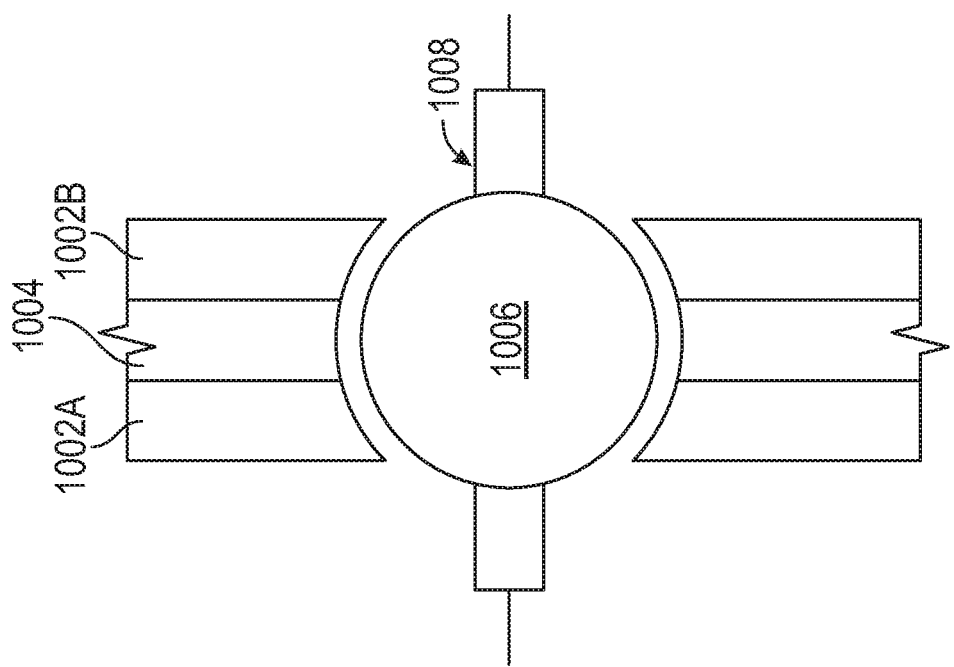

FIGS. 13A and 13B depict how a needle guide 1006 may be locked in a desired position, according to one embodiment. As discussed above, needle guide 1006 may be formed from a deformable material, e.g. plastic. The second layer 1004 is movable relative to the first layers 1002A and 1002B such that two portions of the second layer 1004 located on opposite sides of the needle guide 1006 may impinge on the needle guide 1006 with sufficient force to deform needle guide 1006, as shown in FIG. 13B. When the second layer 1004 impinges upon needle guide 1006, the friction there between prevents further rotation by the needle guide 1006. Thus, the angular position of the needle guide 1006 and, by extension, the needle insertion cylinder 1008 is fixed.

Figure 14:
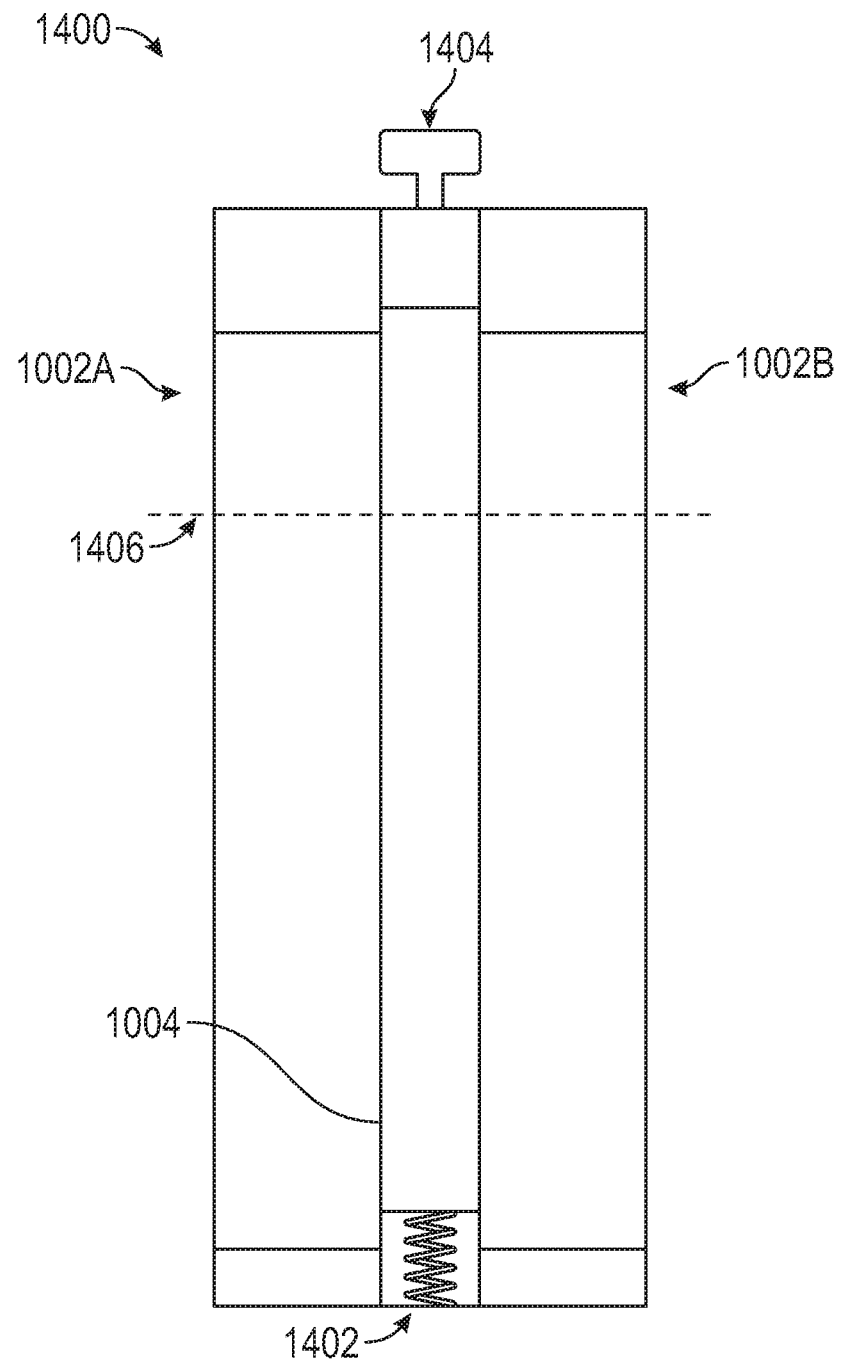
FIG. 14 shows a frame containing the multilayered brachytherapy template shown in FIG. 10A.

FIG. 14 illustrates a frame 1400 for holding the first layers 1002A and 1002B and the second layer 1004. As explained above, the second layer 1004 is located in between the first layers 1002A and 1002B and is movable relative to those layers. As shown in FIG. 14, the frame 1400 includes a biasing mechanism 1402 in the form of a spring that impinges on a bottom portion of the second layer 1004 and biases the second layer in the vertical direction. The top portion of the second layer 1004, on an opposite side of the second layer 1004 from the bottom portion, is connected to an actuator 1404. By depressing the actuator 1404, the second layer 1004 is forced in a downward direction relative to the frame, causing the biasing mechanism 1402 to be compressed. Depressing actuator 1404 can also bring the aperture 1206 of the second layer 1004 (see FIG. 12C) into coaxial alignment with apertures 1008A and 1008B of the first layers 1002A and 1002B. When the first layers 1002A and 1002B and the second layer 1004 are brought into coaxial alignment, the needle guides 1006 become movable and can thus be set at any angular range desired. A needle 1406 may then be inserted through the first layers 1002A and 1002B and the second layer 1004. Releasing the actuator 1404 brings the first layers 1002A and 1002B and the second layer 1004 into a state of misalignment. In the state of misalignment, the second layer 1004 impinges on the needle guides 1006 and thus prevents further rotational motion. Thus, by actuation of the actuator 1404, the template 1000 can be brought into two operative states. In the first state, when the actuator 1404 is released, the needle guides 1006 are incapable of moving, and in the second state the needle guides 1006 are moveable. The biasing mechanism 1402 actively displaces second layer 1004 and thus the default state of the template 1000 is the first state where the needle guides 1006 are incapable of moving. Once the needles are inserted into the body, the body itself acts as a holder and thus even if the actuator is depressed the needle guides 1006 remain immovable.

Figure 15:
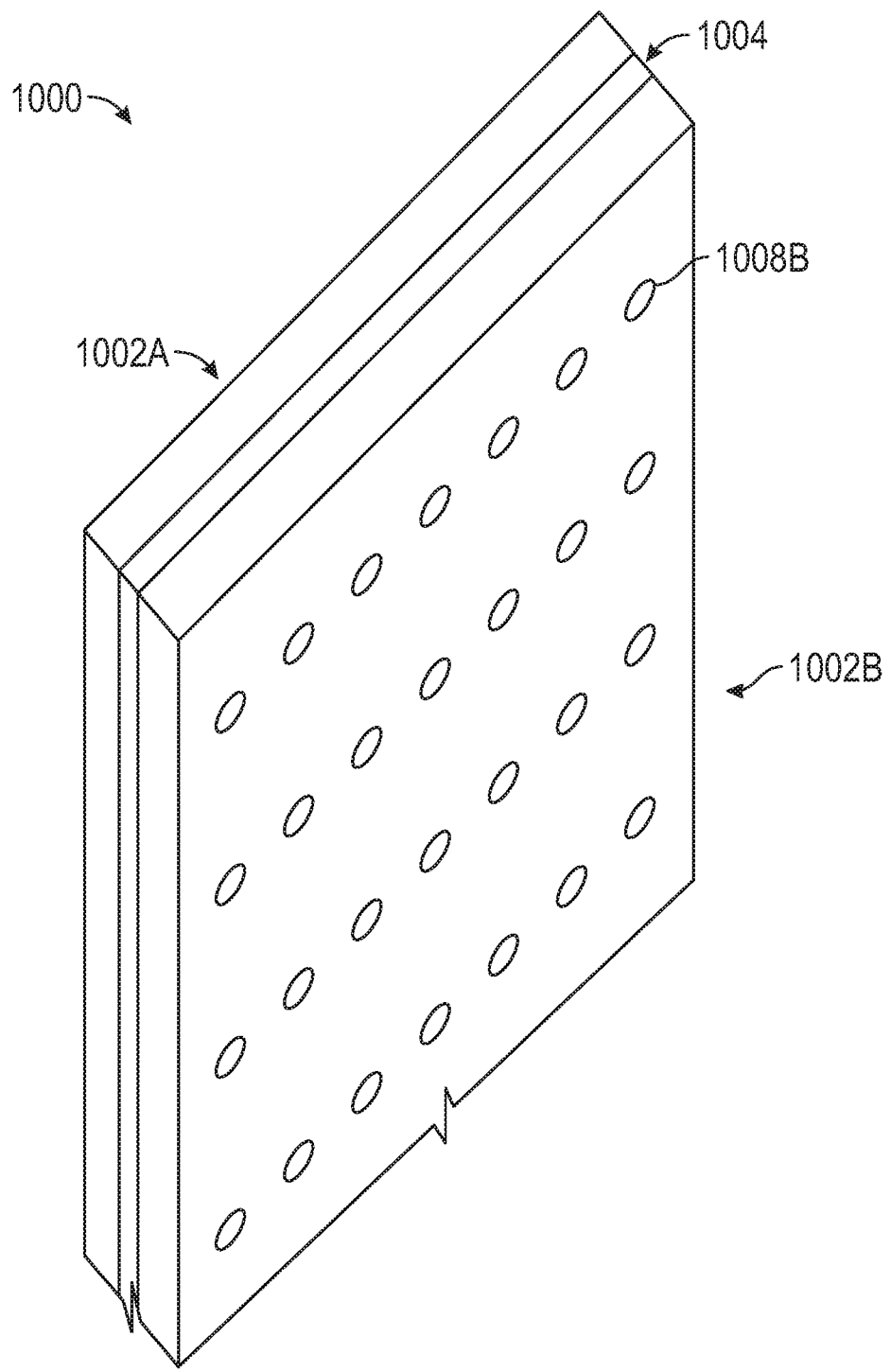
FIG. 15 shows an illustration of a perspective view of the multilayered brachytherapy template shown in FIG. 10A.

FIG. 15 is a perspective view of the template 1000. As shown in FIG. 15, the plurality of apertures 1008B are arranged in a rectangular grid pattern and spaced apart from each other by approximate 0.5 cm.

Various examples of aspects of the disclosure are described below as clauses for convenience. These are provided as examples, and do not limit the subject technology.

Clause A. A brachytherapy template holder, comprising: a template compartment retainer constructed to hold a brachytherapy template, and a perineum attachment component connected to the template compartment retainer by a connecting portion, wherein the perineum attachment component includes a perineum attachment portion formed from a flexible material.

Clause B. A brachytherapy template, comprising: a disposable portion that includes an aperture layer that includes first apertures and a patient contact layer that includes an adhesive on a surface thereof, wherein the patient contact layer is formed from a flexible material.

Clause C. A brachytherapy template, comprising: first layers, each of the first layers includes first apertures, a second layer, arranged between the first layers, that includes second apertures, wherein the first apertures and the second apertures define sockets, and needle guides respectively disposed in the sockets, wherein the needle guides are pivotable by ±20° relative to a longitudinal axis extending from a surface of one of the first layers.

In one or more aspects, examples of additional clauses are described below.

Element 1: the perineum attachment portion includes adhesive application areas formed of a material capable of bonding with an adhesive.

Element 2: the template compartment retainer includes a first opening and the perineum attachment portion includes a second opening, and wherein a cross-sectional area of the second opening is equal to or greater than a cross-sectional area of the first opening.

Element 3: a brachytherapy template comprising apertures, wherein the brachytherapy template is disposed within the template compartment retainer such that longitudinal axes of the apertures are within the first opening and the second opening.

Element 4: displacing rods connected to the perineum attachment portion, wherein the template compartment retainer includes apertures constructed to receive the displacing rods respectively.

Element 5: locking members respectively corresponding to the displacing rods, wherein the locking members are configured to secure the displacing rods relative to the apertures.

Element 6: distal ends of the template compartment retainer and the perineum attachment component, relative to the connecting portion, are closer to each other than proximate ends of the template compartment retainer and the perineum attachment component, relative to the connecting portion.

Element 7: the disposable portion further includes attachment posts connected to the aperture layer.

Element 8: a reusable portion that includes a first aperture plate that includes second apertures.

Element 9: a surface of the first aperture plate lies in a substantially flat plane.

Element 10: a housing, a second aperture plate that includes third apertures, and a third aperture plate that includes fourth apertures, wherein the first aperture plate, the second aperture plate, and the third aperture plate are partially retained in the housing.

Element 11: the second aperture plate and the third aperture plate are movable relative to each other.

Element 12: a first cam system connected to the second aperture plate, a first locking knob connected to the first cam system, a second cam system connected to the third aperture plate, and a second locking knob connected to the second cam system, wherein rotation of the first locking knob operates the first cam system to displace the second aperture plate, and wherein rotation of the second locking knob operates the second cam system to displace the third aperture plate.

Element 13: when the first locking knob is fully rotated, the second aperture plate is at a maximum displacement and the first cam system is in an engaged position where additional rotational force must be applied to the first locking knob to displace the second aperture plate, and when the second locking knob is fully rotated, the third aperture plate is at a maximum displacement and the second cam system is in an engaged position where additional rotational force must be applied to the second locking knob to displace the third aperture plate.

Element 14: threaded receptacles constructed to receive the attachment posts, respectively, and adjustment knobs respectively corresponding to the attachment posts, wherein the adjustment knobs are respectively connected to the attachment posts such that rotation of an adjustment knob causes a corresponding attachment post to advance or retract from a corresponding receptacle.

Element 15: each of second apertures is pivotable by ±20°, inclusive, relative to longitudinal axis extending from a surface of the first aperture plate.

Element 16: second apertures are cylindrical openings in balls, each of the balls being mounted in a corresponding socket connected to the first aperture plate.

Element 17: a locking mechanism configured to lock at least one of second apertures in place.

Element 18: the aperture layer is a curved surface.

Element 19: second apertures are substantially coaxial with first apertures.

Element 20: the second layer is movable relative to the first layers.

Element 21: movement of the second layer relative to the first layers causes the second layer to impinge on the needle guides.

Element 22: the second layer is biased by a biasing mechanism.

Element 23: the biasing mechanism is a spring.

Element 24: an actuator constructed to, upon actuation, cause the second layer to move relative to the first layers and compress the biasing mechanism.

Element 25: the actuation of the actuator moves the second layer relative to the first layers such that the first apertures and the second apertures are coaxial.

Element 26: each of the first apertures includes a conical portion and spherical portion.

Element 27: the spherical portion is hemispherical.

Element 28: the spherical portion is partially spherical.

Element 29: the first layers are symmetrical to each other with respect to a plane defined by the second layer.

Element 30: the needle guides are spherical.

Element 31: the needle guides further comprise a needle insertion cylinder.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A brachytherapy template, comprising:
   first layers, each of the first layers includes first apertures;
   a second layer, arranged between the first layers, that includes second apertures,
   wherein the first apertures and the second apertures define sockets; and
   needle guides respectively disposed in the sockets,
   wherein the needle guides are pivotable by ±20° relative to a longitudinal axis extending from a surface of one of the first layers, and
   wherein the needle guides are independently pivotable with respect to each other.

2. The brachytherapy template of claim 1, wherein the second layer is movable relative to the first layers.

3. The brachytherapy template of claim 2, wherein movement of the second layer relative to the first layers causes the second layer to impinge on the needle guides.

4. The brachytherapy template of claim 2,
   wherein: the second layer is biased by a biasing mechanism; and the brachytherapy template further comprises an actuator constructed to, upon actuation, cause the second layer to move relative to the first layers and compress the biasing mechanism, wherein the actuation of the actuator moves the second layer relative to the first layers such that the first apertures and the second apertures are coaxial.

5. The brachytherapy template of claim 1, wherein:
   each of the first apertures includes a conical portion and a spherical portion, and
   wherein the spherical portion is hemispherical or partially spherical;

the first layers are symmetrical to each other with respect to a plane defined by the second layer;
at least a portion of each of the needle guides is spherical; and
the needle guides further comprise a needle insertion cylinder.

\* \* \* \* \*